United States Patent
Riley, Jr. et al.

(10) Patent No.: US 7,064,835 B2
(45) Date of Patent: Jun. 20, 2006

(54) MINIATURE GAS CELL WITH FOLDED OPTICS

(75) Inventors: William J. Riley, Jr., South Hamilton, MA (US); Robert Lutwak, Marblehead, MA (US)

(73) Assignee: Symmetricom, Inc., Beverly, MA (US)

(*) Notice: Subject to any disclaimer, the term of this patent is extended or adjusted under 35 U.S.C. 154(b) by 384 days.

(21) Appl. No.: 10/653,376

(22) Filed: Sep. 2, 2003

(65) Prior Publication Data

US 2005/0046851 A1    Mar. 3, 2005

(51) Int. Cl.
    *G01B 9/00*    (2006.01)
(52) U.S. Cl. .................................................. 356/437
(58) Field of Classification Search .................. None
    See application file for complete search history.

(56) References Cited

U.S. PATENT DOCUMENTS

| 5,327,105 A | 7/1994 | Liberman et al. |
| 5,340,986 A * | 8/1994 | Wong ......................... 250/343 |
| 6,265,945 B1 | 11/2001 | Delaney et al. |
| 6,320,472 B1 | 11/2001 | Vanier |
| 6,353,225 B1 | 3/2002 | Strzoda et al. |
| 2002/0163394 A1 | 11/2002 | Hollberg et al. |

OTHER PUBLICATIONS

J. Vanier and C. Audoin, "The Quantum Physics of Atomic Frequency Standards," Adam Hilger, Bristol and Philadelphia, 1989, ISBN 0-85274-434-X.

R.H. Dicke, "The Effect of Collisions Upon the Doppler Width of Spectral Lines," Phys. Rev. Lett. vol. 89, pp. 472-473, 1953.

N. Cyr, M. Tetu and M. Breton, "All-Optical Microwave Frequency Standard: A Proposal," IEEE Trans. Instrum. Meas., vol. 42, No. 2, pp. 640-649, Apr. 1993.

S. Knappe, V. Velichansky, H. Robinson, J. Kitching, L. Hollberg, "Atomic Vapor Cells for Miniature Frequency References," Proc. 17th European Frequency and Time Forum and 2003 IEEE International Frequency Control Symposium, May 2003 (to be published).

(Continued)

*Primary Examiner*—Gregory J. Toatley, Jr.
*Assistant Examiner*—Amanda Merlino
(74) *Attorney, Agent, or Firm*—Brinks Hofer Gilson & Lione

(57) ABSTRACT

A miniature optical system for use in instruments based on laser spectroscopy of atomic and molecular samples, such as atomic frequency standards and magnetometers. The miniature optical system employs a folded optical path that allows light from a laser diode to pass through the cell twice, reflecting from a mirror and returning to a photodetector co-located with the laser diode. This efficient packaging arrangement allows the laser diode and photodetector to be fabricated on the same semiconductor substrate and allows essentially all of the gas cell volume to be utilized, without additional optical components for collimation. Fabrication of the laser source and detector on a single substrate permits cost-effective batch processing and parallel testing of the key active components.

41 Claims, 2 Drawing Sheets

OTHER PUBLICATIONS

J. Kitching, S. Knappe, N. Vukićević, R. Wynands, and W. Weidmann, "A Microwave Frequency Reference Based on VCSEL-Driven Dark-Line Resonances in Cs Vapor," IEEE Trans. Instrum. Meas., vol. 49, No. 6, pp. 1313-1317, Dec. 2000.

J. Vanier, M. Levine, D. Janssen and M. Delany, "The Coherent Population Trapping Passive Fequency Standard," IEEE Trans. Instrum. Meas., vol. 52, No. 2, pp. 258-262, Apr. 2003.

* cited by examiner

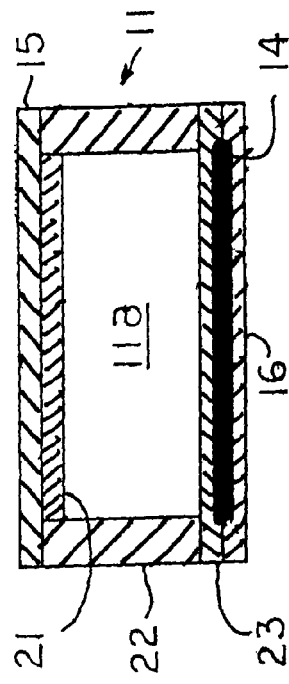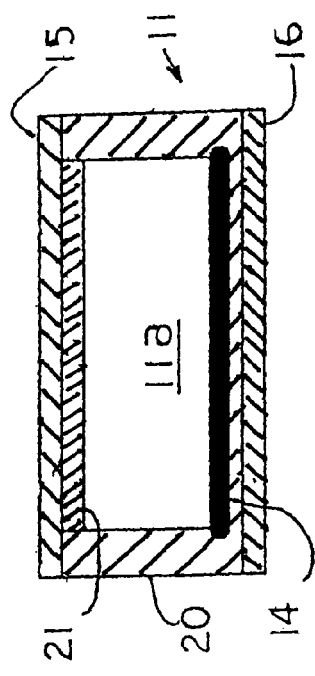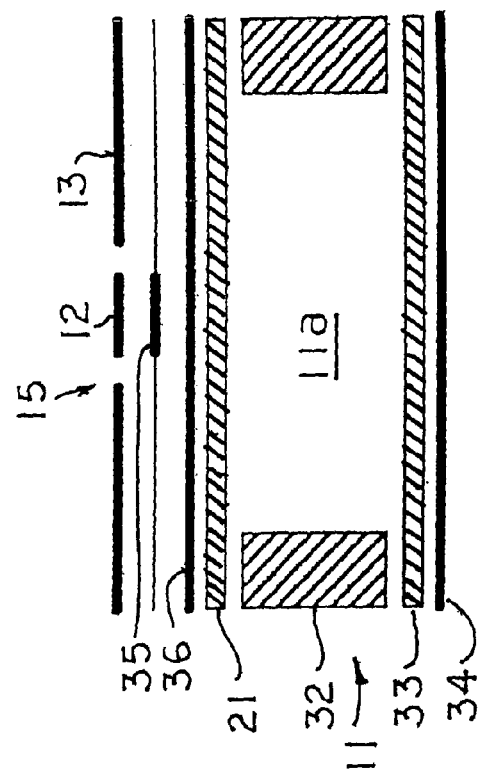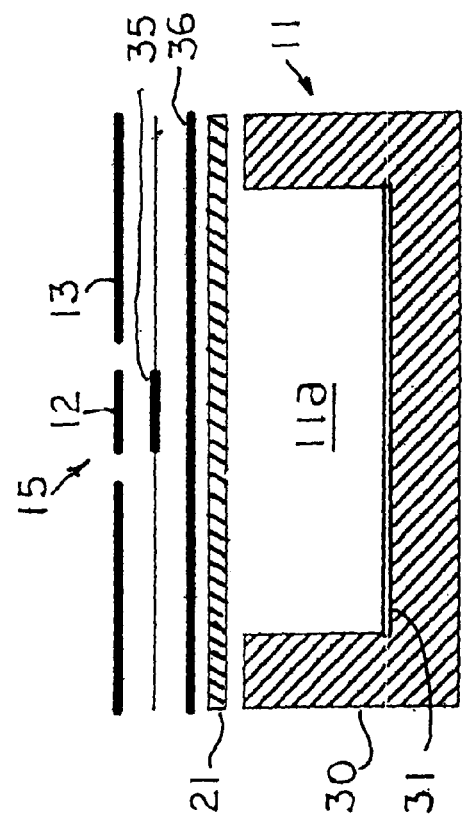
Figure 3a
Figure 3b
Figure 4a
Figure 4b

MINIATURE GAS CELL WITH FOLDED OPTICS

FIELD OF THE INVENTION

The invention relates to the fields of atomic frequency standards and atomic magnetometry. In particular, the invention relates to a physics package of a miniature gas cell atomic frequency standard.

BACKGROUND OF THE INVENTION

Precise spectroscopic interrogation of the resonance features of confined atomic samples can be employed to build atomic frequency standards. As the need for compact, low-power frequency standards has grown, there has been increased emphasis on reducing the size, complexity, and cost of such devices. In particular, the development of reliable, low-power diode lasers has enabled the development of compact, portable atomic instrumentation.

The technology of gas cell atomic frequency standards is well known (see J. Vanier and C. Audoin, *The Quantum Physics of Atomic Frequency Standards*, Adam Hilger, Bristol and Philadelphia, 1989, ISBN 0-85274-434-X), and such devices have been in widespread use for many years. The existing art employs a vapor cell containing an alkali metal, typically rubidium or cesium, along with a buffer gas (see R. H. Dicke, "The Effect of Collisions Upon the Doppler Width of Spectral Lines," *Phys. Rev. Lett.* Vol. 89, pp. 472–473, 1953), which is illuminated by either a discharge lamp or laser diode. The cell's optical transmission displays a narrow resonance feature when it is placed within a microwave cavity and energy is applied at the ground state hyperfine frequency. This response serves as a discriminator to lock the frequency of the microwave source, thereby producing a stabilized output.

In another embodiment, employing the technique of coherent population trapping (CPT), the microwave cavity is eliminated and instead the laser diode is modulated at one-half of the atomic hyperfine frequency (see N. Cyr, M. Têtu, and M. Breton, "All-Optical Microwave Frequency Standard: A Proposal," *IEEE Trans. Instrum. Meas.*, Vol. 42, No. 2, pp. 640–649, April 1993; J. Kitching, S. Knappe, N. Vukićević, R. Wynands and W. Weidmann, "A Microwave Frequency Reference Based on VCSEL-Driven Dark-Line Resonances in Cs Vapor," *IEEE Trans. Instrum. Meas.*, Vol. 49, No. 6, pp. 1313–1317, Dec. 2000; and J. Vanier, M. Levine, D. Janssen and M. Delaney, "The Coherent Population Trapping Passive Frequency Standard," *IEEE Trans. Instrum. Meas.*, Vol. 52, No. 2, pp. 258–262, April 2003), providing an all-optical device that is much smaller, lower in power, and less expensive to produce. (See S. Knappe, V. Velichansky, H. Robinson, J. Kitching, L. Hollberg, "Atomic Vapor Cells for Miniature Frequency References," *Proc. 17th European Frequency and Time Forum and 2003 IEEE International Frequency Control Symposium*, May 2003). In particular, the gas cell can be made using the batch processing methods of micro-machining and micro-electromechanical systems (MEMS) technology. (See U.S. Patent Application No. 2002/0163394, L. Hollberg et al., "Miniature Frequency Standard Based on All Optical Excitation and a Micro-Machined Containment Vessel," Nov. 7, 2002). As the size of the contained volume is reduced, it becomes increasingly necessary that the auxiliary components, including the optical source and detector, heaters and temperature control, and microwave assemblies, be reduced in size and complexity as well.

U.S. Pat. Nos. 6,265,945 and 6,320,472, along with "A Microwave Frequency Reference Based on VCSEL-Driven Dark Line Resonance in Cs Vapor," by J. Kitching et al., and "The Coherent Population Trapping Passive Frequency Standard," by J. Vanier et al. (more completely identified above) describe the principles of building an atomic frequency standard based on coherent population trapping (CPT). U.S. Patent Application No. 2002/0163394 and "Atomic Vapor Cells for Miniature Frequency References" by S. Kappe et al. (identified above) describe the design and fabrication of miniature gas cells for use in such an atomic frequency standard. U.S. Pat. No. 5,327,105 describes a small gas cell that contains a reflective optical path, with a mirror and beam splitter in a common optical configuration for coupling to a photodetector. U.S. Pat. No. 6,353,225 is representative of prior art devices in centimeter size dimensions that employ a laser diode and photodetector to measure the transmission of light through a gas, sensing its response at a particular atomic or molecular absorption line. The disclosed apparatus includes a separate laser diode and separate photodetector located in the same plane and a mirror.

Notwithstanding the developments and prior apparatus described above, there remains a desire and need for more compact, less complex and less expensive atomic frequency standards.

SUMMARY OF THE INVENTION

The present invention provides a chip scale atomic frequency standard, two orders of magnitude smaller and lower in power than the existing technology, and enables wafer-scale production of integrated laser/detector assemblies for atomic frequency standards.

The invention provides a gas cell for interrogation of an atomic gas by means forming a closed gas cell containing an atomic gas sample and carrying a light source and light sensor, and a light reflective surface so the light source, light reflective surface and light sensor form a multiple light path through the atomic gas. In a preferred optical system of the invention for interrogating the gaseous sample, a semiconductor laser is substantially surrounded by a photodetector in an assembly, which is mounted in opposition to a light reflective surface, thereby forming a multiple light path between the laser, the light reflective surface and the photodetector and a compact gas interrogation means. The means forming the gas cell can take many forms, but a preferred form comprises a glass cell or silicon with a light reflective surface carried by its closed end and with its open end being closed by a glass window that carries a single, substantially coplanar semiconductor chip which forms both the semiconductor laser and a surrounding photodetector.

Other features and advantages of the invention are illustrated by the drawings and the more detailed description of the invention that follows.

BRIEF DESCRIPTION OF THE DRAWINGS

FIG. 3a is a cross-sectional view taken at a plane including the central axis of a gas cell of the invention which is formed with a glass or silicon cup having internal light-reflecting surface, and is closed at its open end by a glass window;

FIG. 3b is a cross-sectional view, taken at a plane including the central axis of another gas cell of the invention, formed with a cylindrical sidewall that is closed at both ends by glass windows;

FIG. 4a is a broken-away, cross-sectional view, taken at a plane including the central axis of the gas cell, of a preferred embodiment of the invention for a chip-scale atomic frequency standard where the gas cell is formed with a glass or silicon cup; and FIG. 4b is a broken-away, cross-sectional view, taken at a plane including the central axis of the gas cell where the gas cell is formed with a cylindrical side element closed by two glass end walls.

DETAILED DESCRIPTION OF A PREFERRED EMBODIMENT OF THE INVENTION

The embodiments illustrated and described herein are intended to exemplify the invention in a currently known preferred embodiments, and are not intended to limit the invention, which may be incorporated into embodiments other than those illustrated and described.

Figure 2:
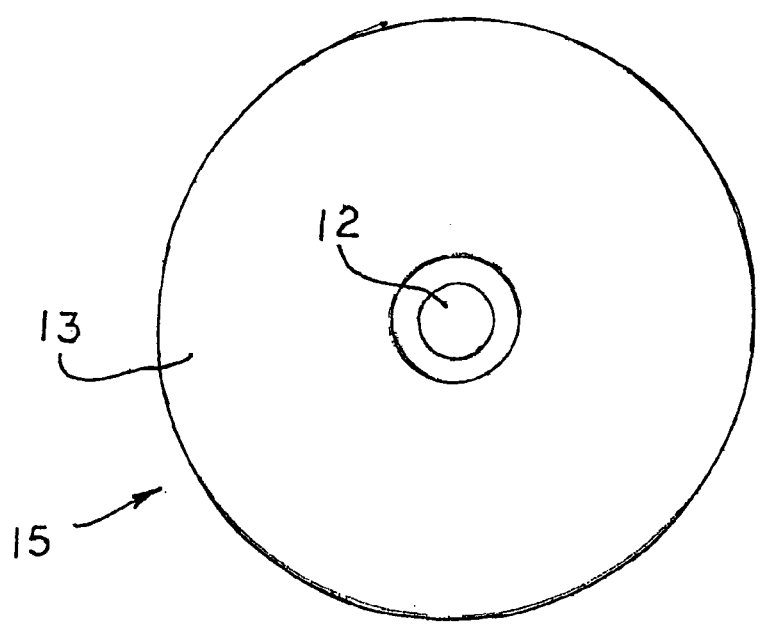
FIG. 2 is a view of the co-located light source and light sensor of the gas cell of FIG. 1 taken at a plane through line 2—2 of FIG. 1 parallel to the surface of the co-located light source and light sensor.
Figure 1:
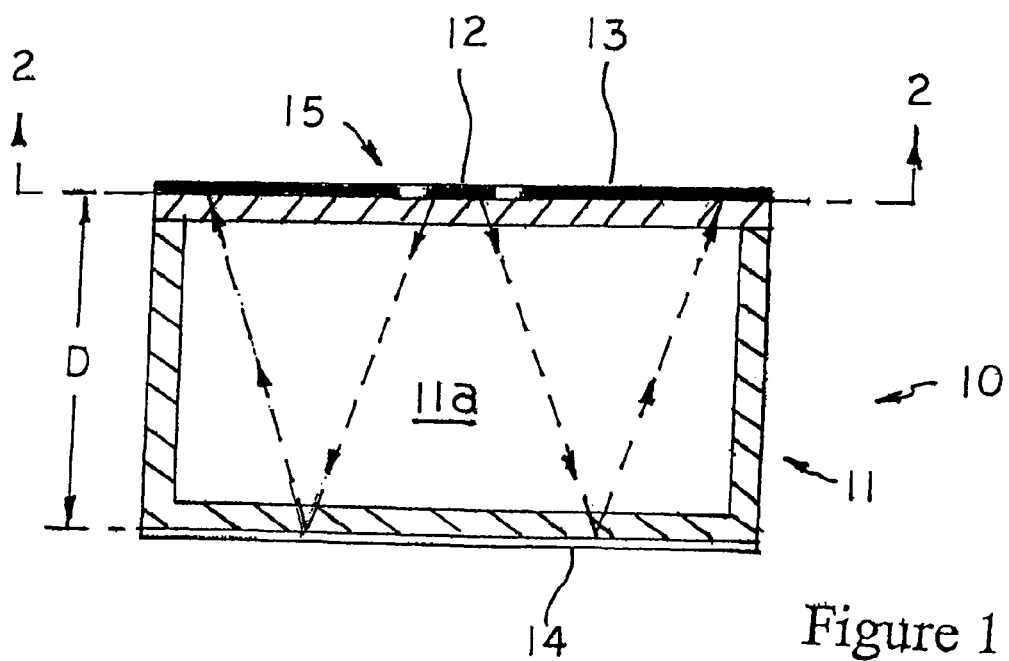
FIG. 1 is a cross-sectional view of a gas cell of the invention taken at a plane including the central axis of the gas cell.

FIG. 1 is a cross-sectional view of a gas interrogation apparatus 10 of the invention for the interrogation of an atomic gas. The gas interrogation apparatus 10 comprises means 11 forming a closed gas cell 11a for containing an atomic gas, such as cesium or rubidium. The means 11 carries a light source 12 and a light sensor 13, which, in the gas interrogation apparatus 10 of FIG. 1, are carried at one end of the means 11. The means 11 also carries a light reflective surface 14, which, in the gas interrogation apparatus 10 of FIG. 1, is carried at the end of means 11, opposite from the end carrying the light source 12 and light sensor 13. As illustrated by FIG. 1 and the dashed lines and arrows, the light source 12, light reflective surface 14 and light sensor 13 form a multiple light path through the atomic gas contained by the closed gas cell 11a formed by means 11. As illustrated by FIGS. 1 and 2, the light source 12 and light sensor 13 may be co-located on a single substrate 15. In a preferred embodiment, the light source 12 and light sensor 13 comprise a semiconductor laser 12 substantially surrounded by a photodetector 13, as illustrated in FIG. 2, and may be formed on a single chip. The semiconductor light source 12 is, preferably, a vertical cavity surface emitting laser (VCSEL) semiconductor laser diode. In the preferred embodiment, the VCSEL and photodiode are fabricated simultaneously on a common substrate although it is possible that, for certain applications, it may be necessary to independently fabricate the laser and detector of incompatible materials prior to assembly.

As illustrated in FIG. 1, the divergent laser beam emerges from the VCSEL 12 and passes through the atomic sample before reaching the reflector 14. Upon reflection, the laser beam then passes through the atomic sample a second time before reaching the detector 13. The spacing between the laser/detector assembly 12, 13, 15 and the reflector 14, as well as the outer diameter of the annular detector 13, are preferably chosen to optimize the collection of the returned light for a given divergence angle from the VCSEL laser 12.

FIGS. 3a and 3b show two preferred means for forming the closed gas cell 11. The gas cell forming means shown in FIGS. 3a and 3b provide MEMS-compatible geometries for the cell body, one a cup 20 with an internal mirror 14 (FIG. 3a) and the other a cylinder 22 with a second window 23 and either an internal mirror or an external mirror 14 (FIG. 3b). FIG. 3b illustrates the mirror 14 external of the cell cavity 11a. Both of these embodiments have a top window 21 to seal the cell, above which is located the laser/detector substrate 15. The means forming the closed gas cell 11 may also have heaters and temperature sensors 16 to elevate and control the temperature of the cell. Typically in an atomic frequency standard or magnetometer, the gaseous sample is contained in a cell 11, FIGS. 3a and 3b, which is made from silicon sealed with a glass window or windows using an anodic bonding process, and the laser diode/photodetector assembly 12, 13, 15 is located above the top window 21. The bottom reflecting surface 14 is made of copper or another alkali-compatible material, and is either placed on to the bottom of a silicon cup 20, or onto the inside or outside of a second glass window 23 anodically bonded onto the bottom of a cylindrical silicon body. In the case of the external mirror, its chemical compatibility with the atomic gas is not critical. While silicon has been used typically as described above, an all-glass cell may be used instead in the invention.

FIGS. 4a and 4b show detailed assemblies of particular preferred embodiments of the invention, broken away to better illustrate the elements of the assembly. FIGS. 4a and 4b illustrate preferred embodiments for a chip-scale atomic frequency standard based on the technique of coherent population trapping (CPT). The cell is comprised of a silicon or glass cup 30 with a mirrored bottom 31 as shown in FIG. 4a, or a silicon or glass cylinder 32 with a mirrored window 33, 34 as shown in FIG. 4b. The VCSEL/detector assembly 12, 13, 15 is mounted atop the cell, along with an optical attenuator 35 and quarter-wavelength optical phase retarder ($\lambda/4$-plate) 36 between the laser 12 and the top window 21. The attenuator 35 sets the optimum light intensity and provides optical isolation to protect against back reflections into the laser 12. The quarter wave plate 36 converts the linearly polarized laser beam to circular polarization as required for the CPT interrogation. One or more of these additional optical elements can be integrated with the window 21 or wit the laser/photodetector assembly 12, 13, 15 to simplify the design and reduce assembly steps. The cell cavity 11a is filled with a small amount of cesium or rubidium alkali metal gas plus an inert buffer gas or buffer gas mixture. In FIG. 4b, the cell is made from an envelope forming the periphery of the cell. e.g., a silicon or glass cylinder 32, sealed wit glass windows 21, 33 at both the top and bottom. Although the mirror 34 is shown on the outside of the bottom window 33 in FIG. 4b, in this arrangement the mirror surface 34 can be deposited on either the inside or outside of the second window 33. In all cases, a heater and temperature sensor (not shown in FIG. 4a and 4b, but see FIGS. 3a and 3b) is located at the bottom of the cell 11 to maintain the cell at the proper operating temperature. As an alternative, the cell 11 may use an internal wall coating in the cavity 11a instead of, or in addition to, the buffer gas to narrow the width of the resonance line. An important detail is that the handedness of the circular polarization, as measured along the propagation direction of the light, is reversed upon reflection from the mirror of the folded optical path, but the rotation of the field, as observed by the atomic sample, is unchanged, as required by the CPT interrogation method.

A principal advantage of the folded optical path of the invention is to allow the two semiconductor devices (laser diode and photodetector) to be integrated together at one end of the cell. This makes the design compact, simplifies the construction of the device, and allows heater and temperature sensor components to be located at the bottom of the cell. The simultaneous epitaxy of construction of a vertical-cavity surface emitting laser (VCSEL) and a resonant-cavity enhanced photodetector is practical and effective. The divergence angle of the laser diode 12, and the shape of the mirror 14, is made such that the reflected light fills the sensitive area of the photodetector. This provides the additional advantage of fully utilizing the volume of the cell cavity 11a and increasing its effective length by causing the reflected light to pass through different atoms within the cell, thus allowing the cell to be made smaller. Each laser/detector pair 12, 13 can be tested, prior to dicing and packaging, by energizing the VCSEL devices 12, at the wafer level, and measuring the signal of the photodetector 13, when a reflector is placed parallel to the wafer surface.

The invention thus provides a compact optical system combining a vertical-cavity surface-emitting laser (VCSEL) 12 co-located on a common substrate 15 with an optical power detector (photodiode) 13, and a mirror 14, which reflects the divergent laser beam onto the detector, as exemplified in FIG. 1. Preferably, the VCSEL and detector are arranged in an annular geometry as shown in FIG. 2, and a gaseous atomic sample is located in a cavity 11a between the laser/detector assembly 12, 13, 15 and the mirror 14 so the divergent laser beam passes through the gaseous atomic sample, is reflected by the mirror, passes through the sample again, and strikes the detector 13. In atomic frequency standards and magnetometers of the invention, the gaseous atomic sample may be sealed within a gas cell, which can be in the form of either a cup or a cylinder, with a window at either the top or both the top and bottom, and with the VCSEL and photodetector at one end and the mirror at the other end, as set forth above.

Those skilled in the art will recognize that embodiments of the invention other than those illustrated and described herein can be devised, and that the invention is only limited by the scope of the claims and the prior art.

What is claimed is:

1. An optical system for interrogating a gaseous sample, comprising
   a) a semiconductor laser substantially surrounded by a photodetector in a laser/photodetector assembly;
   b) a reflective surface mounted in opposition to said laser/photodetector assembly, wherein light emitted by said laser is directed through said gaseous sample at least twice, thereby forming a compact gas interrogation means.

2. The optical system of claim 1 wherein said semiconductor laser and photodetector are co-located on a single substrate.

3. The optical system of claim 1 wherein the semiconductor laser and photodetector are a substantially coplanar assembly and the distance between the substantially coplanar assembly and the reflective surface optimizes the return of light to the photodetector.

4. An optical system of claim 1 wherein the optical system comprises a further reflective surface providing an optical path that traverses said gaseous sample an even number of times that is greater than two.

5. An optical system of claim 1 wherein said semiconductor laser is a vertical cavity surface-emitting laser diode (VCSEL).

6. An optical system of claim 1 wherein said gaseous sample is contained within a sealed gas cell with an optically transparent window.

7. The optical system of claim 6 wherein said sealed gas cell comprises a cup with said reflective surface on its bottom.

8. The optical system of claim 7 wherein said optically transparent window is glass that is anodically bonded to the open end of said cup.

9. The optical system of claim 6 wherein said sealed gas cell comprises a cylinder with a bottom window providing said reflective surface.

10. The optical system of claim 6 wherein said gas cell comprises a cylinder with a glass top and bottom windows that are anodically bonded to the ends of said cylinder, said top glass window carrying said laser/photodetector assembly and said bottom glass window carrying said reflective surface.

11. The optical system of claim 6 wherein said sealed gas cell carries a heater and temperature sensor.

12. The optical system of claim 1 in which said gaseous sample is an atomic gas located between said laser/photodetector assembly and said reflective surface, and in which microwave excitation is additionally introduced into said gaseous sample to resonantly excite the ground state hyperfine transition in interrogating said gaseous atomic sample.

13. The optical system of claim 1 further comprising a quarter-wave plate to circularly polarize the light emission of said semiconductor laser, and in which said gaseous atomic sample is an atomic gas located between said laser photodetector assembly and said reflective surface, the ground-state hyperfine frequency of said gaseous atomic sample being interrogated by means of microwave modulation applied to said laser at an even sub-harmonic thereof.

14. The optical system of claim 1 in which said atomic gaseous sample is located between said laser/photodetector assembly and said reflective surface, and in which audio frequency radiation is resonantly applied to measure magnetic field strength by the technique of Zeeman resonance spectroscopy.

15. In an atomic frequency standard containing an optically reactive gas, the improvement comprising means for providing multiple light paths through said optically reactive gas, including a concentrically assembled semiconductor laser and photodetector and a reflective surface, with a closed gas cell containing said optically reactive gas therebetween, said gas cell having dimensions such that divergent light of said laser optimally impinges on said photodetector.

16. In an atomic magnetometer containing an optically reactive gas, the improvement comprising a means for providing multiple light paths through said optically reactive gas, including concentrically assembled semiconductor laser/photodetector devices and a reflective surface, with a closed gas cell containing the optically reactive gas, therebetween, said gas cell having dimensions such that divergent light of said laser optimally impinges on said photodetector.

17. A gas cell for interrogation of an atomic gas, comprising
   means forming a closed gas cell containing the atomic gas,
   said means carrying a light source and a light sensor formed on a single substrate, and further carrying a light reflective surface, said light source, fight reflective surface, and light sensor forming a multiple light path through the atomic gas in said closed gas cell,
   light from said light source traveling through the closed gas cell and being reflected from said light reflective surface to said light sensor.

18. The gas cell of claim 17 wherein said means forming a closed gas cell comprises a light transparent window carrying said single substrate formed with a laser diode and a photodetector for sensing the emission of the laser diode.

19. The gas cell of claim 18 wherein the means forming the closed gas cell comprises a glass or silicon cup with a cylindrical periphery and a closed end, with said light reflective surface carried by the closed end of said cup.

20. The gas cell of claim 19 wherein the light reflective surface is a mirror formed on the outside of the bottom closed end.

21. The gas cell of claim 17 wherein the means forming a closed gas cell carries a heater.

22. The gas cell of claim 19 further comprising an integrated heater and temperature sensor carried by said closed end.

23. The gas cell of claim 17 wherein the atomic gas comprises cesium gas.

24. The gas cell of claim 17 wherein the atomic gas comprises rubidium gas.

25. A gas cell for interrogation of an atomic gas, comprising
means forming a closed gas cell including the atomic gas;
an envelope forming the periphery of the gas cell,
a transparent window closing one end of the envelope and carrying a substantially coplanar substrate carrying a light source and a light sensing detector, and
means closing the other end of the envelope and carrying a light reflective surface
said light source, light reflective surface, and light sensing detector forming a multiple light path through the atomic gas in said closed gas cell, light from said light source traveling through the closed gas cell and being reflected from said light reflective surface to said light sensing detector.

26. The gas cell of claim 18 further comprising a quarter wave plate to circularly polarize the light emission of said laser diode.

27. The gas cell of claim 18 further comprising an optical attenuator for the light emission of said laser diode.

28. Means forming a gas cell for an atomic frequency standard, said means comprising
a cup-shaped glass container forming the periphery and one end of the gas cell, said one end of the gas cell carrying a light reflective surface, and an integrated heater and temperature sensor,
a glass window sealed with the periphery of the cup-shaped glass container, closing and forming the other end of the gas container,
a single chip formed with a semiconductor laser diode and a photodetector carried by said glass window, said single chip and said light reflective surface being spaced by said cup-shaped container so light from the semiconductor laser diode can be directed at said light reflective surface and reflected from said light reflective surface to optimally impinge on said photodetector.

29. The means of claim 28 further comprising an optical attenuator and a quarter wave plate positioned between said semiconductor laser diode and the interior of said cup-shaped glass container.

30. In a CPT atomic frequency standard including a closed gas cell containing an atomic gas, the improvement comprising
means forming a multiple path for light through the atomic gas, including a concentrically assembled light source and light detector, and a light reflective surface, and
a circular polarizer for the light from said light source, said circularly polarized light traveling through the atomic gas in said gas cell and being reflected from said light reflective surface to said light detector.

31. The improvement of claim 30 wherein the light source comprises a semiconductor laser and wherein the semiconductor laser and light detector are a substantially coplanar assembly.

32. The improvement of claim 31 wherein, the semiconductor laser and light detector are formed on a single substrate.

33. The improvement of claim 30 wherein the distance between the concentrically assembled light source and light detector and the light reflective surface optimizes the return of light to the light detector.

34. The improvement of claim 30 wherein the means forming a multiple path through the atomic gas provides an optical path that traverses the atomic gas an even number of times that is greater than two.

35. The improvement of claim 30 wherein said light source comprises a vertical cavity surface-emitting laser diode (VCSEL).

36. The improvement of claim 30 wherein said closed gas cell includes an optically transparent window through which said light travels.

37. The improvement of claim 36 wherein said closed gas cell comprises a cup with said reflective surface on its closed bottom.

38. The improvement of claim 37 wherein said optically transparent window is glass that is anodically bonded to the open end of said cup.

39. The improvement of claim 36 wherein said closed gas cell comprises a cylinder with a bottom window providing said reflective surface.

40. The improvement of claim 30 wherein said closed gas cell comprises a cylinder with glass top and bottom windows that are anodically bonded to the ends of said cylinder, said top glass window carrying said light source and light detector and said bottom glass window carrying said light reflective surface.

41. The improvement of claim 30 wherein said closed gas cell carries a heater and temperature sensor.

* * * * *

UNITED STATES PATENT AND TRADEMARK OFFICE
CERTIFICATE OF CORRECTION

| | | |
|---|---|---|
| PATENT NO. | : 7,064,835 B2 | Page 1 of 1 |
| APPLICATION NO. | : 10/653376 | |
| DATED | : June 20, 2006 | |
| INVENTOR(S) | : William J. Riley, Jr. and Robert Lutwak | |

It is certified that error appears in the above-identified patent and that said Letters Patent is hereby corrected as shown below:

Face Page
Item (56) - After 6,265,945 B1, delete "11/2001" and insert -- 7/2001 --.

Column 6
Line 7, delete "scaled" and insert -- sealed --.
Line 62, delete "fight" and insert -- light --.

Column 7
Line 10, delete "bottom".

Signed and Sealed this

Fifteenth Day of August, 2006

JON W. DUDAS
*Director of the United States Patent and Trademark Office*